United States Patent
Takahashi

(10) Patent No.: US 11,098,701 B2
(45) Date of Patent: *Aug. 24, 2021

(54) VARIABLE-STIFFNESS ACTUATOR

(71) Applicant: OLYMPUS CORPORATION, Tokyo (JP)

(72) Inventor: Masaya Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 471 days.

This patent is subject to a terminal disclaimer.

(21) Appl. No.: 15/986,895

(22) Filed: May 23, 2018

(65) Prior Publication Data

US 2018/0266402 A1 Sep. 20, 2018

Related U.S. Application Data

(63) Continuation of application No. PCT/JP2015/083648, filed on Nov. 30, 2015.

(51) Int. Cl.
*F03G 7/06* (2006.01)
*A61B 1/00* (2006.01)
(Continued)

(52) U.S. Cl.
CPC .......... *F03G 7/065* (2013.01); *A61B 1/0051* (2013.01); *A61B 1/0058* (2013.01);
(Continued)

(58) Field of Classification Search
CPC .. F03G 7/065; F03G 7/06; F16F 1/021; F16F 1/041; F16F 2224/0258; A61B 1/00078; A61B 1/0051; A61B 1/0058; A61B 1/128
See application file for complete search history.

(56) References Cited

U.S. PATENT DOCUMENTS 4,601,283 A 7/1986 Chikama
4,930,494 A * 6/1990 Takehana ........... A61B 1/00147
600/145
(Continued)

FOREIGN PATENT DOCUMENTS

JP S58-101601 U 7/1983
JP S61-100392 A 5/1986
(Continued)

OTHER PUBLICATIONS

International Search Report dated Feb. 16, 2016 issued in PCT/JP2015/083648.
(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A variable-stiffness actuator includes a shape-memory member that increases in stiffness on heating, a heating member arranged to surround the shape-memory member along a longitudinal axis of the shape-memory member, and a heat transmitting medium arranged to surround the heating member along a longitudinal axis of the heating member. The heating member generates heat in response to supply of a current, so as to heat the shape-memory member. The heat transmitting medium is deformed to decrease an inner diameter of the heat transmitting medium to come into contact with the heating member, so as to cool the heating member. The heat transmitting medium is deformed to increase the inner diameter to come out of contact with the heating member.

8 Claims, 13 Drawing Sheets

(51) Int. Cl.
*A61B 1/005* (2006.01)
*F16F 1/02* (2006.01)
*A61B 1/12* (2006.01)
*F16F 1/04* (2006.01)

(52) U.S. Cl.
CPC .......... *A61B 1/00078* (2013.01); *A61B 1/128* (2013.01); *F03G 7/06* (2013.01); *F16F 1/021* (2013.01); *F16F 1/041* (2013.01); *F16F 2224/0258* (2013.01)

(56) References Cited

U.S. PATENT DOCUMENTS

| | | | | |
|---|---|---|---|---|
| 4,987,314 | A * | 1/1991 | Gotanda | A61B 1/0058 250/551 |
| 5,055,101 | A * | 10/1991 | McCoy | A61B 1/0051 604/528 |
| 5,090,956 | A * | 2/1992 | McCoy | A61B 1/0051 600/434 |
| 5,482,029 | A | 1/1996 | Sekiguchi et al. | |
| 8,075,476 | B2 * | 12/2011 | Vargas | A61B 1/00154 600/114 |
| 10,485,400 | B2 * | 11/2019 | Hakkens | A61L 29/126 |
| 2006/0064055 | A1 * | 3/2006 | Pile-Spellman | A61M 25/0105 604/95.05 |
| 2015/0282693 | A1 * | 10/2015 | Hakkens | A61M 25/0158 604/95.05 |
| 2017/0321666 | A1 * | 11/2017 | Morishima | A61B 1/0055 |

FOREIGN PATENT DOCUMENTS

| | | |
|---|---|---|
| JP | H6-292652 A | 10/1994 |
| JP | H7-39586 A | 2/1995 |
| JP | 3122673 B2 | 1/2001 |
| JP | 3142928 B2 | 3/2001 |
| JP | 2004-150283 A | 5/2004 |
| JP | 2005-046273 A | 2/2005 |
| JP | 2011-194126 A | 10/2011 |

OTHER PUBLICATIONS

English Abstract of JP H05-91971 A, dated Apr. 16, 1993.
English Abstract of JP H05-168586 A, dated Jul. 2, 1993.
English translation of International Preliminary Report on Patentability dated Jun. 14, 2018 together with the Written Opinion received in related International Application No. PCT/JP2015/083648.

* cited by examiner

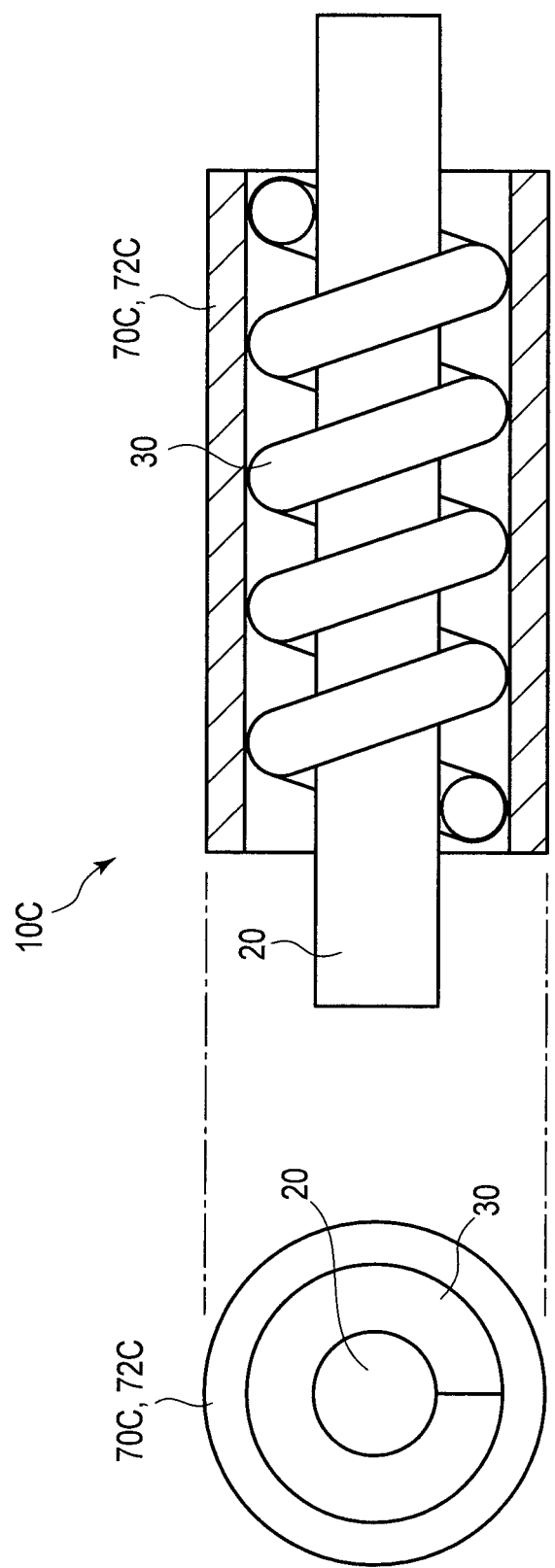
F I G. 13

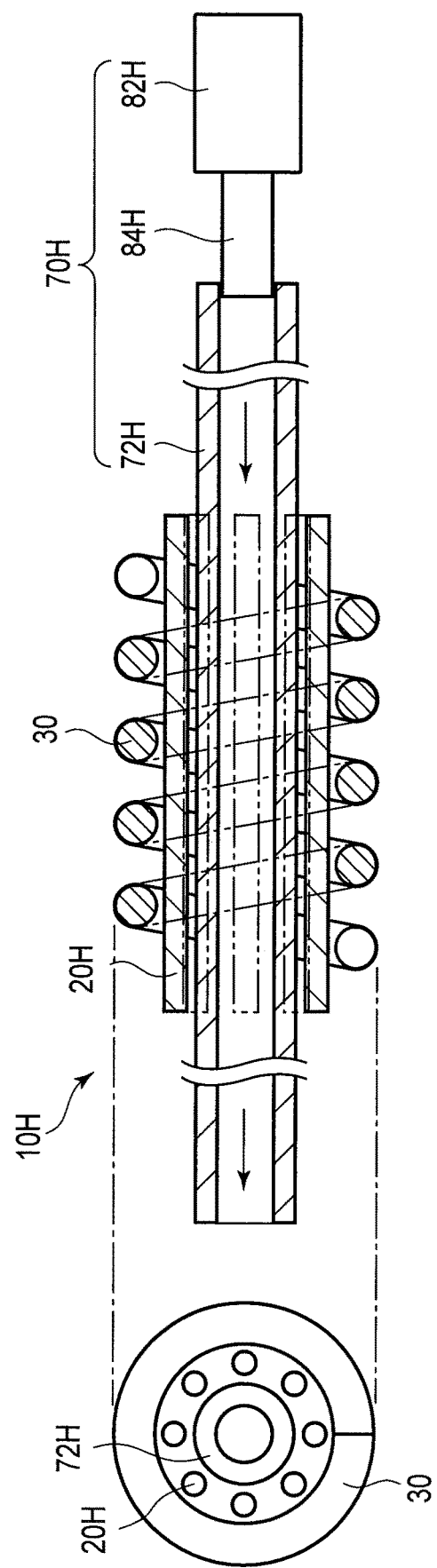
F I G. 18

VARIABLE-STIFFNESS ACTUATOR

CROSS-REFERENCE TO RELATED APPLICATIONS

This application is a Continuation Application of PCT Application No. PCT/JP2015/083648, filed Nov. 30, 2015, the entire contents of which are incorporated herein by reference.

BACKGROUND OF THE INVENTION

1. Field of the Invention

The present invention relates to a variable-stiffness actuator for varying the stiffness of a flexible member.

2. Description of the Related Art

Japanese Patent No. 3122673 discloses an endoscope in which the stiffness of a flexible portion of an insertion section may be varied. In this endoscope, a flexible member (for example, a coil pipe) has a front end fixed at a predetermined position in the endoscope, and a rear end fixed to a flexibility adjustment member (for example, a flexibility adjustment wire inserted through a coil pipe) through a separator. The flexible member and the flexibility adjustment member extend to a handling section along the flexible portion and extend over almost the entire flexible portion. The flexible member is compressed and stiffened by pulling the flexibility adjustment member, thereby varying the stiffness of the flexible portion.

Japanese Patent No. 3142928 discloses a variable-stiffness apparatus for flexible tubes using a shape-memory alloy. The variable-stiffness apparatus includes a coil provided in a flexible tube, an electrical insulative tube provided inside the coil, a shape-memory alloyed wire located in the electrical insulative tube to extend in its axial direction, and energization heating means to energize the shape-memory alloyed wire.

The shape-memory alloyed wire has a property of elongating at a low temperature and contracting at a high temperature. The shape-memory alloyed wire extends out through fixed portions at both ends of the coil, and caulking members are fixed to the both ends. The shape-memory alloyed wire is arranged so as to loosen at a low temperature and to tighten up with the caulking members being engaged with the fixed portions at a-high temperature.

The shape-memory alloyed wire contracts to stiffen the coil at a high temperature at which it is heated by the energization heating means. On the other hand, the shape-memory alloyed wire elongates to soften the coil at a low temperature at which it is not energized.

BRIEF SUMMARY OF THE INVENTION

A variable-stiffness actuator includes a shape-memory member that increases in stiffness on heating, a heating member arranged to surround the shape-memory member along a longitudinal axis of the shape-memory member, and a heat transmitting medium arranged to surround the heating member along a longitudinal axis of the heating member. The heating member generates heat in response to supply of a current, so as to heat the shape-memory member. The heat transmitting medium is deformed to decrease an inner diameter of the heat transmitting medium to come into contact with the heating member, so as to cool the heating member. The heat transmitting medium is deformed to increase the inner diameter to come out of contact with the heating member.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 13 shows the variable-stiffness actuator according to the fourth embodiment when the heat transmitting medium is in a second phase.

FIG. 18 shows a variable-stiffness actuator according to a ninth embodiment.

DETAILED DESCRIPTION OF THE INVENTION

First Embodiment

Figure 1:
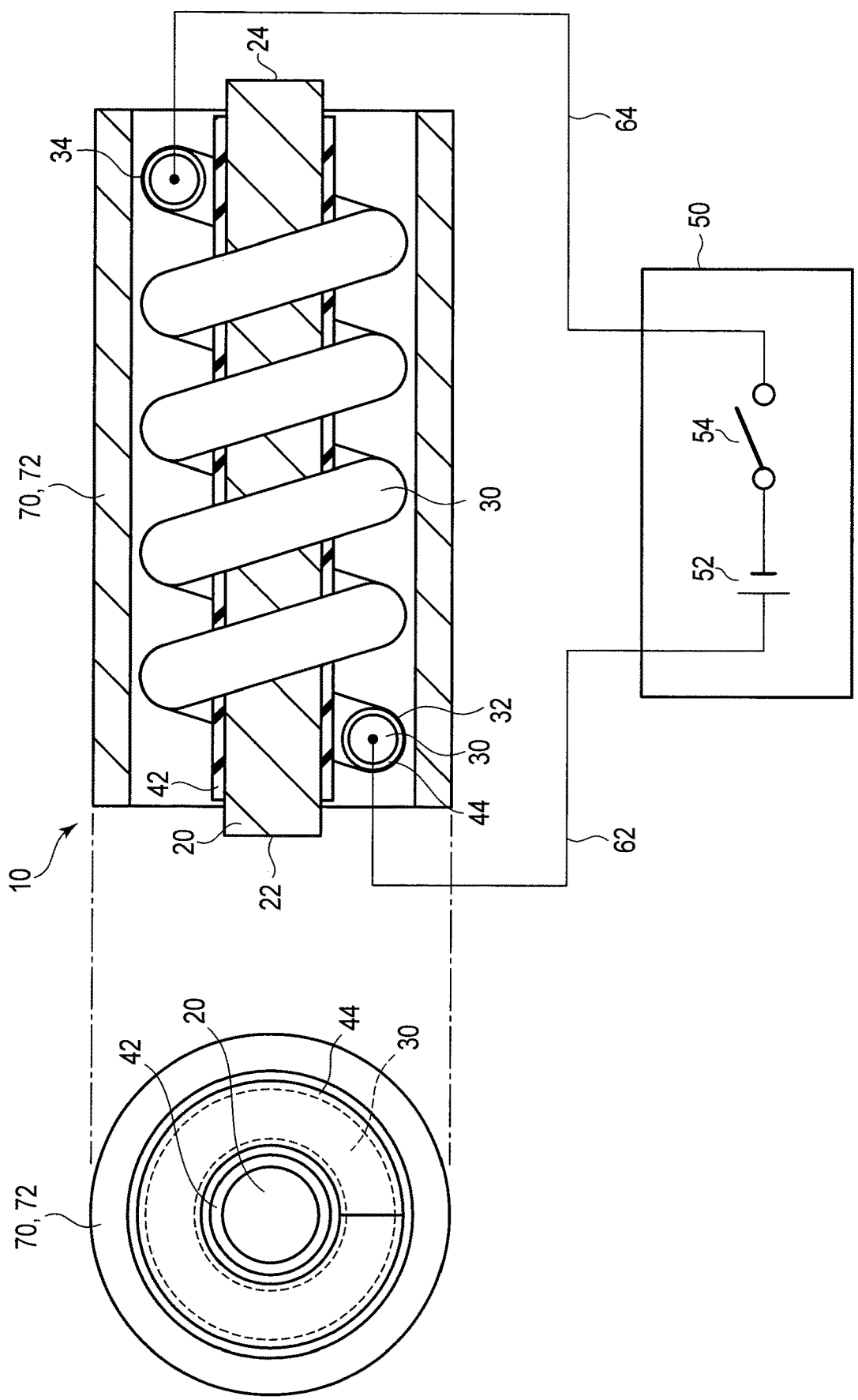
FIG. 1 shows a variable-stiffness actuator according to a first embodiment.

FIG. 1 shows a variable-stiffness actuator according to a first embodiment. A variable-stiffness actuator 10 is installed in a flexible member, and has a function of providing different stiffness for the flexible member by taking different stiffness statuses. As shown in FIG. 1, the variable-stiffness actuator 10 includes a shape-memory member 20 that can transition in phase between a first phase and a second phase and an inducing member 30 that causes a shape-memory member 20 to transition in phase between the first phase and the second phase. The variable-stiffness actuator 10 is arranged in the flexible member so that the shape-memory member 20 has at least one free end. The flexible member may be an exterior covering member of an insertion section of an endoscope.

The shape-memory member 20 takes a flexible state in which the shape-memory member 20 is easily deformable by an external force, namely, exhibits a low elastic modulus, when the shape-memory member 20 is in the first phase, so as to provide lower stiffness to the flexible member. The shape-memory member 20 takes a rigid state in which it tends to take a memorized shape memorized beforehand against an external force, namely, exhibits a high elastic modulus, when it is in the second phase, so as to provide higher stiffness to the flexible member. In particular, the stiffness of the shape-memory member 20 increases on heating. The memorized shape may be, but not limited to, a linear shape.

Herein, the external force means a force that may deform the shape-memory member 20, and gravity is considered to be part of the external force.

The inducing member 30 has a function of generating heat. The shape-memory member 20 has a property of transitioning in phase from the first phase to the second phase in response to the generation of heat of the inducing member 30.

The shape-memory member 20 may be constituted from, for example, a shape-memory alloy. The shape-memory alloy may be alloy including, but not limited to, for example, NiTi. The shape-memory member 20 is not limited to the above, and may also be constituted from a different material, such as a shape-memory polymer, shape-memory gel, or shape-memory ceramics.

The shape-memory alloy constituting the shape-memory member 20 may be, for example, a shape-memory alloy that transitions in phase between a martensitic phase and an austenitic phase. In the martensitic phase, the shape-memory alloy is plastically deformed relatively easily by external force. That is, the shape-memory alloy exhibits a low elastic modulus in the martensitic phase. In the austenitic phase, the shape-memory alloy is not easily deformed by external force. Even when the shape-memory alloy is deformed by greater external force, it exhibits superelasticity and returns to its memorized shape when the greater external force is lost. That is, the shape-memory alloy exhibits a high elastic modulus in the austenitic phase.

The inducing member 30 is constituted from a conductive material, and has a property of generating heat in response to supply of a current. In other words, the inducing member 30 is constituted by a heating member that generates heat in response to supply of a current. The inducing member 30 may be constituted by, for example, a heating wire, namely, a conductive member with large electrical resistance.

The shape-memory member 20 has an elongated exterior shape. The inducing member 30 is constituted by a member shaped like a wire, and is arranged around the shape-memory member 20. The inducing member 30 extends along a longitudinal axis of the shape-memory member 20. The inducing member 30 spirally extends around the shape-memory member 20 along the longitudinal axis of the shape-memory member 20 with an appropriate gap from the shape-memory member 20. This configuration enables efficient conduction of heat generated by the inducing member 30 to the shape-memory member 20.

The shape-memory member 20 may be constituted from a conductive material. For example, the shape-memory member 20 is provided with an insulating film 42 on the circumference. The insulating film 42 serves to prevent a short circuit between the shape-memory member 20 and the inducing member 30. The insulating film 42 is provided to cover at least a portion facing the inducing member 30. FIG. 1 shows a configuration in which the outer peripheral surface of the shape-memory member 20 is partly covered; however, the configuration is not limited to this, and the outer peripheral surface of the shape-memory member 20 may be entirely covered, or the shape-memory member 20 may be entirely covered.

The inducing member 30 is provided with an insulating film 44 on the circumference. The insulating film 44 serves to prevent a short circuit between the shape-memory member 20 and the inducing member 30 and a short circuit between adjacent portions of the inducing member 30.

The shape-memory member 20 has a first end 22 and a second end 24, and the inducing member 30 has a first end 32 located on a side of the first end 22 of the shape-memory member 20 and a second end 34 located on a side of the second end 24 of the shape-memory member 20.

The first end 32 of the inducing member 30 is electrically connected to a controller 50 through a wire 62, and the second end 34 of the inducing member 30 is electrically connected to the controller 50 through a wire 64.

The controller 50 includes a power source 52 and a switch 54. The power source 52 and the switch 54 are connected in series. That is, an end of the power source 52 is connected to an end of the switch 54, the other end of the power source 52 is connected to the wire 62, and the other end of the switch 54 is connected to the wire 64. The controller 50 supplies a current to the inducing member 30 in response to an ON or closing operation of the switch 54, and stops supplying a current to the inducing member 30 in response to an OFF or opening operation of the switch 54. The inducing member 30 generates heat in response to supply of a current.

The variable-stiffness actuator 10 further includes a cooling system 70 that cools the shape-memory member 20. Herein, cooling means promoting heat dissipation from an object; in other words, improving a heat dissipation function of an object.

The cooling system 70 has a heat transmitting medium 72 that promotes heat dissipation from the shape-memory member 20. The heat transmitting medium 72 does not necessarily need to promote heat dissipation from the entire shape-memory member 20, and should promote heat dissipation from at least a part of the shape-memory member 20, for example, a portion corresponding to the inducing member 30. Herein, the portion corresponding to the inducing member 30 means a portion that is heated by the inducing member 30.

Similarly to the shape-memory member 20, the heat transmitting medium 72 is easily deformable by external force. The heat transmitting medium 72 has, for example, an elastic modulus equivalent to that of the shape-memory member 20 in the first phase.

The heat transmitting medium 72 is arranged around the outside of the inducing member 30, and extends along the longitudinal axis of the shape-memory member 20. That is, the heat transmitting medium 72 has a hollow shape such as a cylindrical shape, and the shape-memory member 20 and the inducing member 30 are arranged in an inner space of the heat transmitting medium 72. Such a configuration allows the variable-stiffness actuator 10 to be a very compact structure. Such a structure is favorable for reducing a size in a radial direction.

The heat transmitting medium 72 has heat conductivity higher than that of the shape-memory member 20. For example, the inducing member 30 has heat conductivity higher than that of the shape-memory member 20, and the heat transmitting medium 72 has heat conductivity higher than that of the inducing member 30.

The above-described variable-stiffness actuator 10 is installed in the flexible member without restricting both ends of the shape-memory member 20. For example, the variable-stiffness actuator 10 is arranged in a limited space of the flexible member with a small gap so that an end or both ends of the shape-memory member 20 are a free end or free ends.

Herein, the limited space means space of a right size capable of containing the variable-stiffness actuator 10 therein. Thus, even if deformation of one of the variable-stiffness actuator 10 and the flexible member is slight, it may come into contact with the other to give external force.

For example, the flexible member may be a tube having an inner diameter slightly larger than the outer diameter of the variable-stiffness actuator 10, and the variable-stiffness actuator 10 may be placed inside the tube. The configuration of the flexible member is not limited to this, and the flexible member only has to have a space slightly larger than the variable-stiffness actuator 10.

When the shape-memory member 20 is in the first phase, the variable-stiffness actuator 10 provides relatively lower stiffness to the flexible member, so as to be easily deformed by external force exerted on the flexible member, namely, force capable of deforming the shape-memory member 20.

When the shape-memory member 20 is in the second phase, the variable-stiffness actuator 10 provides relatively higher stiffness to the flexible member, so as to tend to return to its memorized shape against external force exerted on the flexible member, namely, force capable of deforming the shape-memory member 20.

For example, the phase of the shape-memory member 20 is switched between the first and second phases by the controller 50, so that the stiffness of the flexible member is switched.

In addition to switching the stiffness, in a situation where external force is exerted on the flexible member, the variable-stiffness actuator 10 also functions as a bidirectional actuator that switches the shape of the flexible member. In another situation where no external force is exerted on the flexible member, but the flexible member is deformed in the first phase before the phase of the shape-memory member 20 is switched to the second phase, the variable-stiffness actuator 10 also serves as a unidirectional actuator that returns the shape of the flexible member to the original.

Figure 2:
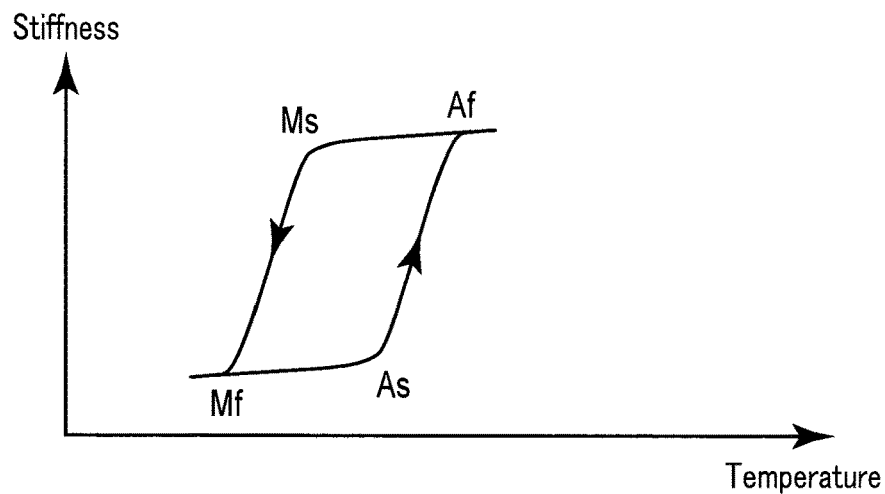
FIG. 2 is a graph showing a stiffness change with respect to a temperature change in a shape-memory member of the variable-stiffness actuator according to the first embodiment.

FIG. 2 is a graph showing the stiffness change with respect to the temperature change in the shape-memory member 20 of the variable-stiffness actuator 10. In FIG. 2, the As point indicates a temperature at which the phase starts to transition from the martensitic phase to the austenitic phase during heating, the Af point indicates a temperature at which the phase finishes transitioning to the austenitic phase during heating, the Ms point indicates a temperature at which the phase starts to transition from the austenitic phase to the martensitic phase during cooling, and the Mf point indicates a temperature at which the phase finishes transitioning to the martensitic phase during cooling. During a transition from the As point to the Af point and during the transition from the Ms point to the Mf point, the martensitic phase and the austenitic phase are mixed. As can be understood from FIG. 2, the locus of the stiffness change during heating is different from the locus of the stiffness change during cooling. That is, the stiffness change with respect to the temperature change of the shape-memory member 20 has a hysteresis.

Figure 3:
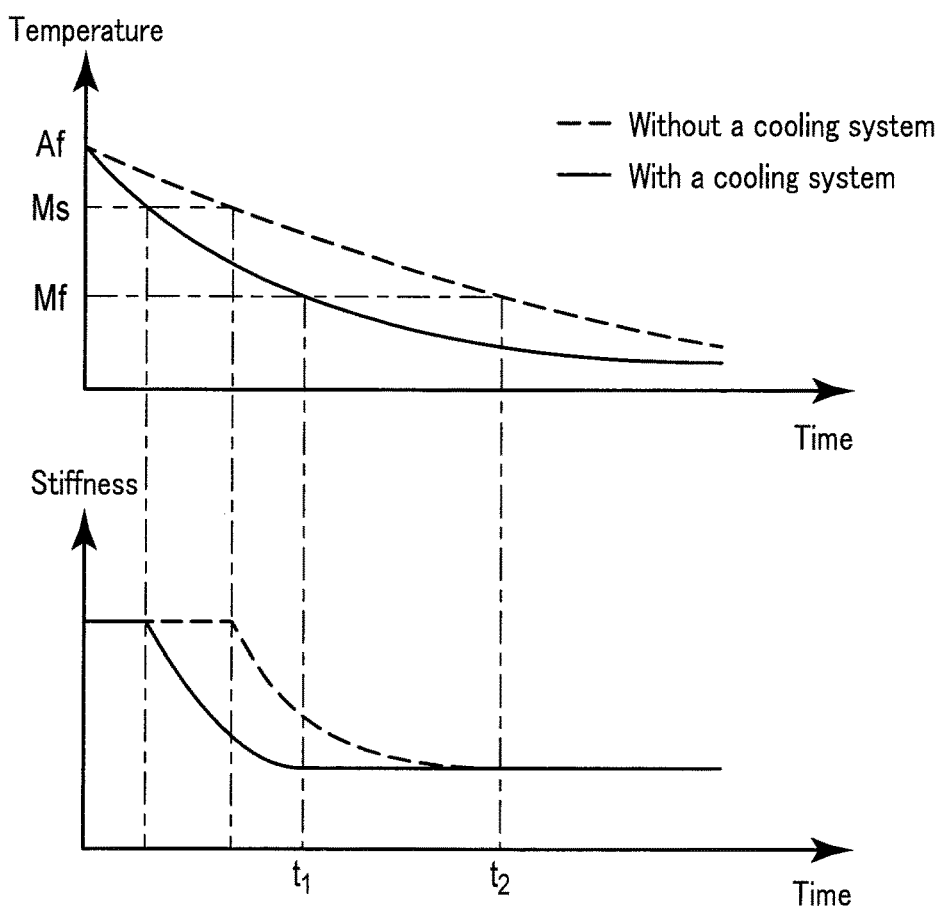
FIG. 3 is a graph showing changes of the temperature and stiffness in the shape-memory member of the variable-stiffness actuator according to the first embodiment with respect to passage of time.

FIG. 3 shows changes of the temperature and the stiffness of the shape-memory member 20 of the variable-stiffness actuator 10 with respect to passage of time during the phase transition from the austenitic phase Af to the martensitic phase Mf. In FIG. 3, changes of the temperature and the stiffness of the shape-memory member 20 in the variable-stiffness actuator 10 of the present embodiment, namely the variable-stiffness actuator 10 having a cooling system, are shown by solid lines. In FIG. 3, as a comparative example, changes of the temperature and the stiffness of a shape-memory member in a variable-stiffness actuator that does not have a cooling system are shown by broken lines.

As shown in FIG. 3, the shape-memory member of the variable-stiffness actuator of the comparative example without a cooling system transitions in phase to the martensitic phase Mf at time t2, while the shape-memory member 20 of the variable-stiffness actuator 10 of the present embodiment with a cooling system transitions in phase to the martensitic phase Mf at time t1(<t2). That is, the shape-memory member 20 of the variable-stiffness actuator 10 of the present embodiment with a cooling system transitions in phase to the martensitic phase Mf in a shorter time than the shape-memory member of the variable-stiffness actuator of the comparative example without a cooling system.

Accordingly, the shape-memory member 20 of the variable-stiffness actuator 10 of the present embodiment with a cooling system changes from the rigid state to the flexible state in a shorter time than the shape-memory member of the variable-stiffness actuator of the comparative example without a cooling system. That is, the variable-stiffness actuator 10 of the present embodiment with a cooling system takes a shorter time to transition from the rigid state to the flexible state than the variable-stiffness actuator of the comparative example without a cooling system.

Thus, compared to the variable-stiffness actuator of the comparative example without a cooling system, the variable-stiffness actuator 10 of the present embodiment with a cooling system is improved in responsivity of switching from the rigid state to the flexible state.

Second Embodiment

FIGS. 4 to 7 show a variable-stiffness actuator according to a second embodiment. In FIGS. 4 to 7, the members identical to those shown in FIG. 1 are assigned the reference numerals identical to those shown in FIG. 1, and the detailed descriptions thereof are omitted. In the drawings of the second and subsequent embodiments, the controller 50, wires 62 and 64, and insulating films 42 and 44 are not shown to simplify the drawings. The following descriptions will be provided with an emphasis on the difference.

Namely, the points that are not mentioned below are the same as those of the first embodiment.

Figure 4:
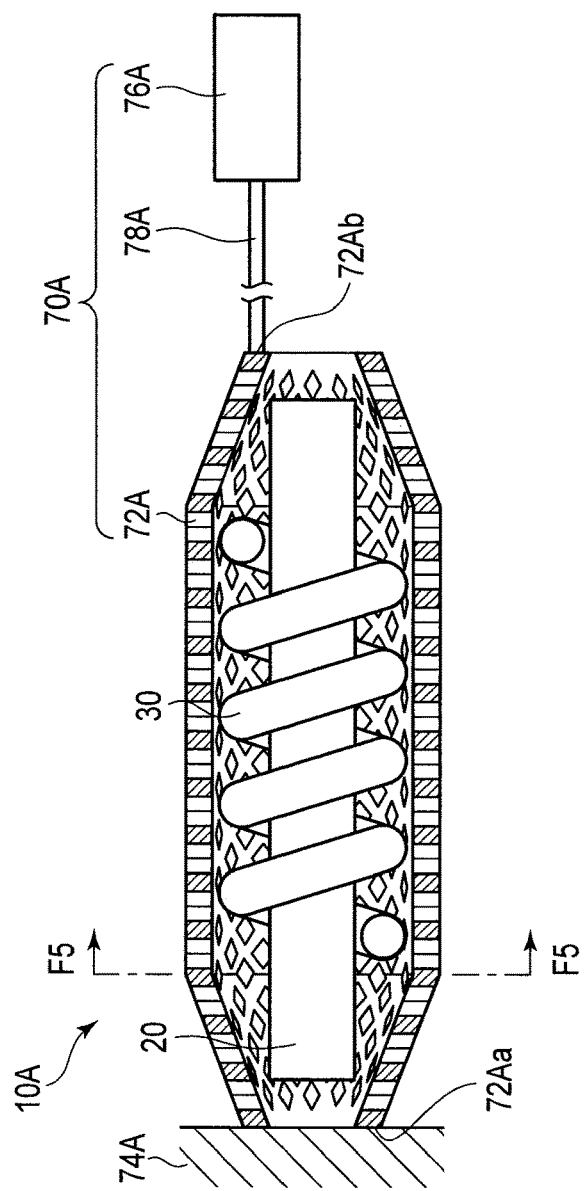
FIG. 4 shows a variable-stiffness actuator according to a second embodiment when a heat transmitting medium is in a non-deformed state.
Figure 5:
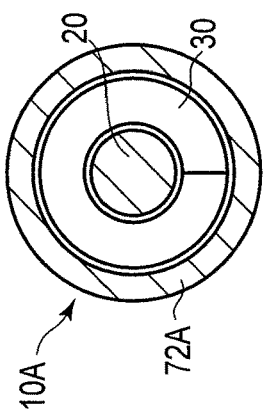
FIG. 5 shows a cross section of the variable-stiffness actuator, taken along line F5-F5 in FIG. 4.
Figure 6:
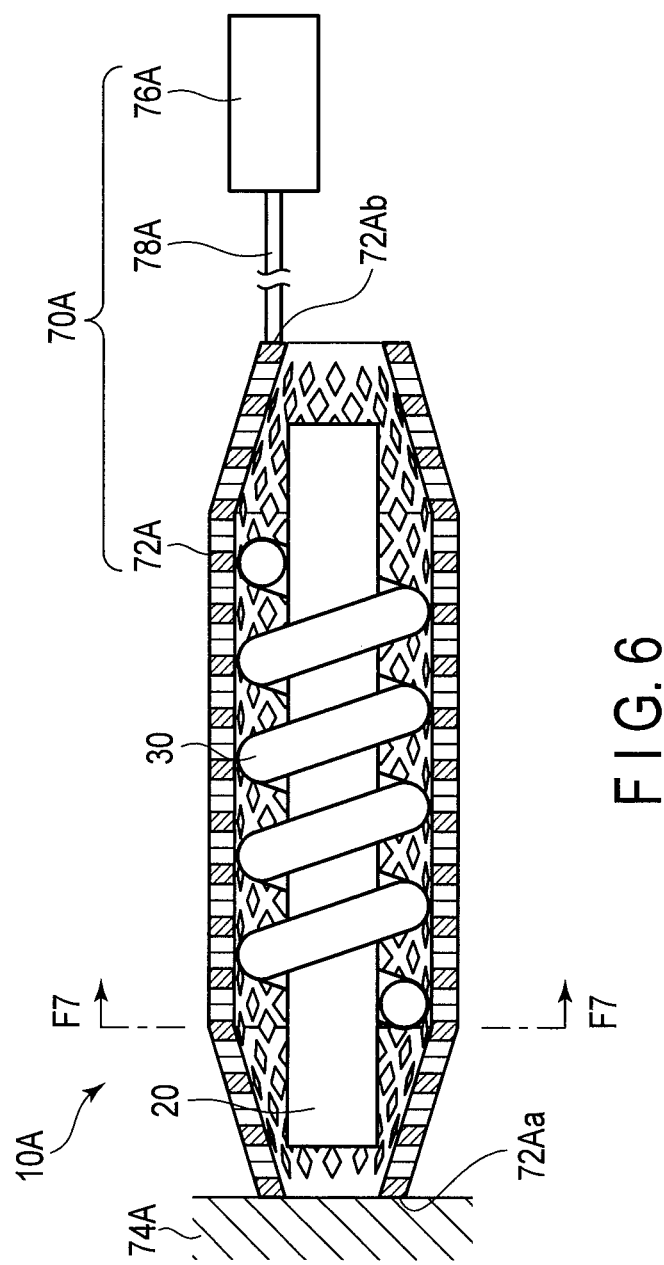
FIG. 6 shows the variable-stiffness actuator according to the second embodiment when the heat transmitting medium is in a deformed state.
Figure 7:
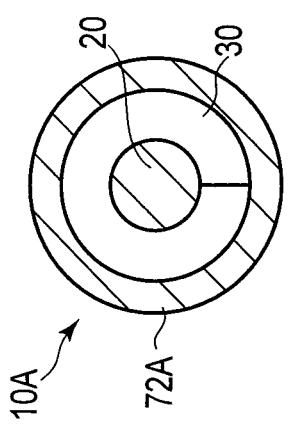
FIG. 7 shows a cross section of the variable-stiffness actuator, taken along line F7-F7 in FIG. 6.

FIG. 4 shows a variable-stiffness actuator 10A when a heat transmitting medium 72A is in a non-deformed state. FIG. 5 shows a cross section of the variable-stiffness actuator 10A, taken along line F5-F5 in FIG. 4. FIG. 6 shows the variable-stiffness actuator 10A when the heat transmitting medium 72A is in a deformed state. FIG. 7 shows a cross section of the variable-stiffness actuator 10A, taken along line F7-F7 in FIG. 6.

The variable-stiffness actuator 10A of the present embodiment includes the shape-memory member 20, the inducing member 30, and a cooling system 70A that cools the shape-memory member 20.

The cooling system 70A includes a heat transmitting medium 72A that promotes heat dissipation from the shape-memory member 20. The heat transmitting medium 72A is arranged around the outside of the inducing member 30, and extends along a longitudinal axis of the shape-memory member 20. That is, the heat transmitting medium 72A has a hollow shape such as a cylindrical shape in which both ends are narrowed, and the shape-memory member 20 and the inducing member 30 are arranged in an inner space of the heat transmitting medium 72A.

The heat transmitting medium 72A has heat conductivity higher than that of the shape-memory member 20. For example, the inducing member 30 has heat conductivity higher than that of the shape-memory member 20, and the heat transmitting medium 72A has heat conductivity higher than that of the inducing member 30.

The heat transmitting medium 72A has elasticity. Thus, the heat transmitting medium 72A is easily deformed when mechanical force is applied, and returns to the original shape when the force is lost. When mechanical force to extend the heat transmitting medium 72A along the longitudinal axis is applied, the heat transmitting medium 72A extends along the longitudinal axis and decreases its diameter. The heat transmitting medium 72A is formed in, for example, a mesh-like shape so as to be easily deformed.

The cooling system 70A further includes a fixing member 74A that fixes a first end 72Aa of the heat transmitting medium 72A, a force generating device 76A that generates mechanical force along the longitudinal axis of the heat transmitting medium 72A, and a force transmitting member 78A that transmits the mechanical force generated by the force generating device 76A to the heat transmitting medium 72A. The force transmitting member 78A is mechanically fixed to a second end 72Ab of the heat transmitting medium 72A, and is moved along the longitudinal axis of the heat transmitting medium 72A by the force generating device 76A. The force transmitting member 78A may be constituted by, for example, wires.

When the heat transmitting medium 72A is in the non-deformed state, there are a gap between the shape-memory member 20 and the inducing member 30, and a gap between the inducing member 30 and the heat transmitting medium 72A, as shown in FIGS. 4 and 5.

If the second end 72Ab of the heat transmitting medium 72A is pulled by the force generating device 76A, the heat transmitting medium 72A is extended and is deformed to decrease its inner diameter. Consequently, the heat transmitting medium 72A comes into contact with the inducing member 30; furthermore, reduction of the diameter of the heat transmitting medium 72A decreases a diameter of the inducing member 30, and then the inducing member 30 comes into contact with the shape-memory member 20. As a result, the gap between the inducing member 30 and the heat transmitting medium 72A and the gap between the shape-memory member 20 and the inducing member 30 disappear, as shown in FIGS. 6 and 7.

In contrast, if the force to pull the second end 72Ab of the heat transmitting medium 72A is lost, the heat transmitting medium 72A shrinks by its restoring force and is deformed to increase the inner diameter, thereby returning to the original shape. As a result, a gap is generated between the shape-memory member 20 and the inducing member 30, and a gap is also generated between the inducing member 30 and the heat transmitting medium 72A, as shown in FIGS. 4 and 5. Accordingly, the heat transmitting medium 72A is no longer in contact with the inducing member 30.

As described above, the cooling system 70A switches a contact or non-contact state of the heat transmitting medium 72A with the inducing member 30 by deforming the heat transmitting medium 72A by applying mechanical force to the heat transmitting medium 72A, more specifically, by changing the diameter of the heat transmitting medium 72A by pulling the heat transmitting medium 72A through the force transmitting member 78A to extend the heat transmitting medium 72A.

The heat dissipation efficiency of the shape-memory member 20 is higher in a situation in which the shape-memory member 20, the inducing member 30, and the heat transmitting medium 72A are mechanically in contact with each other than in a situation in which the shape-memory member 20, the inducing member 30, and the heat transmitting medium 72A are mechanically separate from each other. That is, the heat dissipation efficiency of the shape-memory member 20 is switched by switching a contact or non-contact state of the heat transmitting medium 72A with the inducing member 30 by the cooling system 70A.

When switching the variable-stiffness actuator 10A from a rigid state to a flexible state, the heat transmitting medium 72A is brought into contact with the inducing member 30 by the cooling system 70A, thereby cooling the inducing member 30. Thus, the time required for transition to the flexible state is shortened.

In the present embodiment, since the inducing member 30 is arranged around the outside of the shape-memory member 20, the heat transmitting medium 72A is brought into contact with the inducing member 30 by the cooling system 70A, but the heat transmitting medium 72A may be brought into contact with the shape-memory member 20. Such a configuration is obtained by forming the shape-memory member 20 in a hollow shape and arranging the inducing member 30 in an inner space of the shape-memory member 20.

Third Embodiment

FIGS. 8 to 11 show a variable-stiffness actuator according to a third embodiment. In FIGS. 8 to 11, the members identical to those shown in FIG. 1 are assigned the reference numerals identical to those shown in FIG. 1, and the detailed descriptions thereof are omitted. The following descriptions will be provided with an emphasis on the difference. Namely, the points that are not mentioned below are the same as those of the first embodiment.

Figure 8:
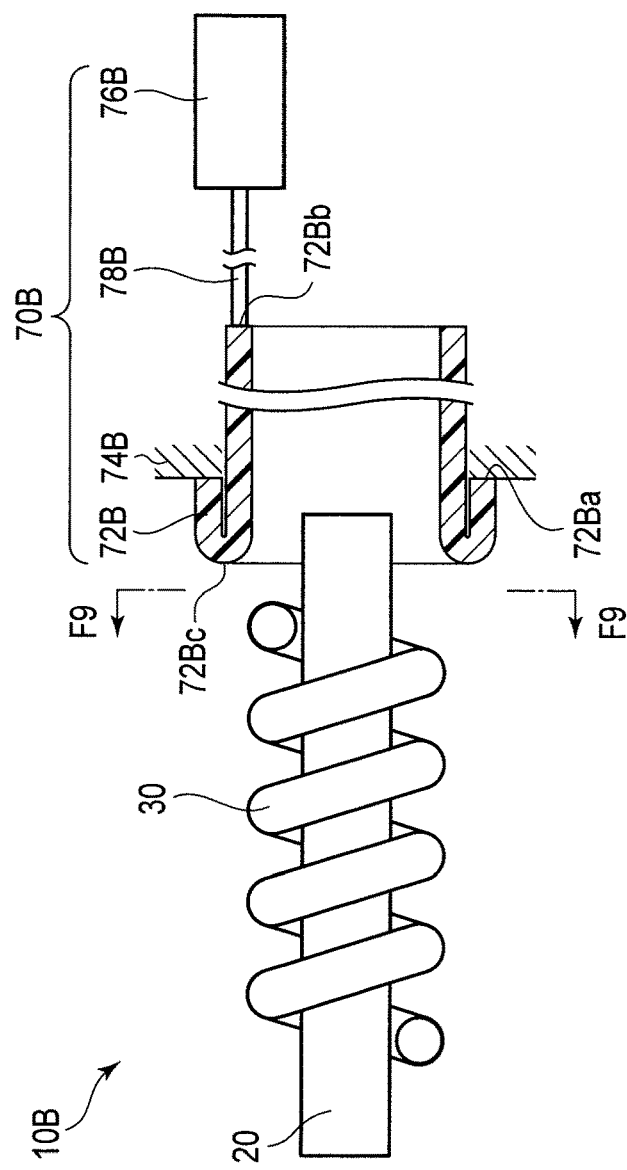
FIG. 8 shows a variable-stiffness actuator according to a third embodiment when a heat transmitting medium is evacuated from an inducing member.
Figure 9:
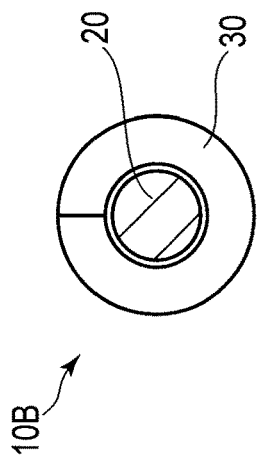
FIG. 9 shows a cross section of the variable-stiffness actuator, taken along line F9-F9 in FIG. 8.
Figure 10:
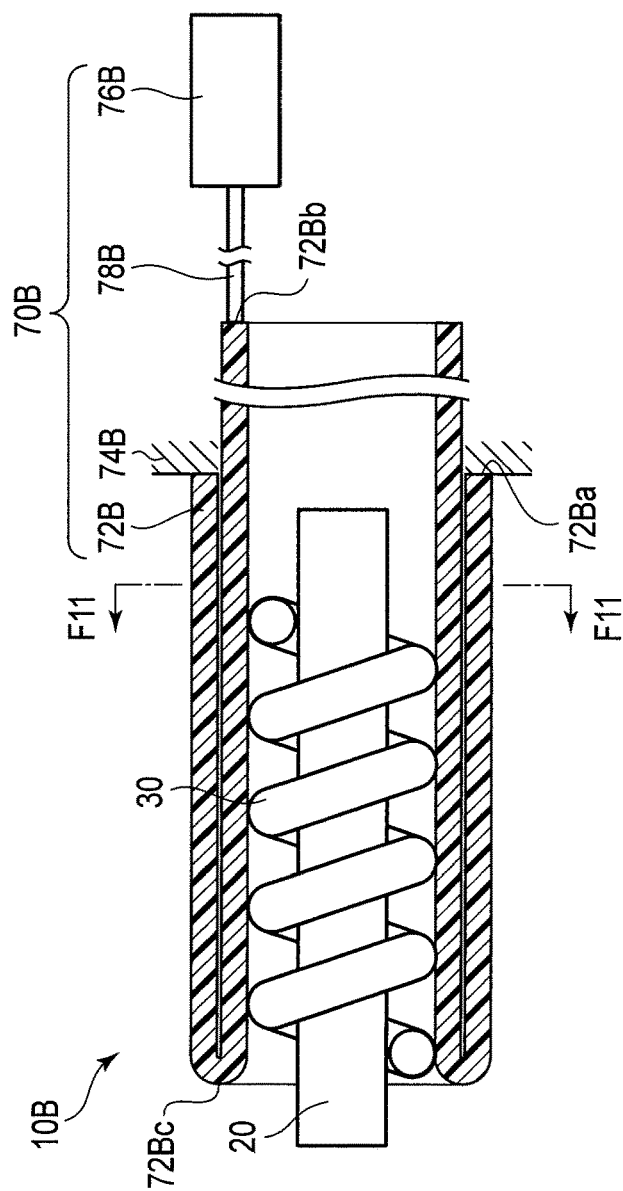
FIG. 10 shows the variable-stiffness actuator according to the third embodiment when the heat transmitting medium covers the inducing member.
Figure 11:
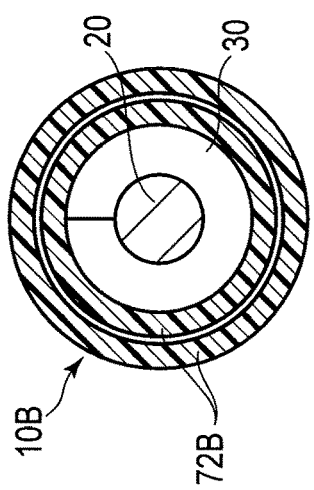
FIG. 11 shows a cross section of the variable-stiffness actuator, taken along line F11-F11 in FIG. 10.

FIG. 8 shows a variable-stiffness actuator 10B when a heat transmitting medium 72B is evacuated from an inducing member 30. FIG. 9 shows a cross section of the variable-stiffness actuator 10B, taken along line F9-F9 in FIG. 8. FIG. 10 shows the variable-stiffness actuator 10B when the heat transmitting medium 72B covers the inducing member. FIG. 11 shows a cross section of the variable-stiffness actuator 10B, taken along line F11-F11 in FIG. 10.

The variable-stiffness actuator 10B of the present embodiment includes the shape-memory member 20, the inducing member 30, and a cooling system 70B that cools the shape-memory member 20.

The cooling system 70B includes a heat transmitting medium 72B that promotes heat dissipation from the shape-memory member 20. The heat transmitting medium 72B has a hollow shape such as a cylindrical shape, which is folded back, and extends along a longitudinal axis of the shape-memory member 20. An inner diameter of the heat transmitting medium 72B is set somewhat smaller than an outer diameter of the inducing member 30.

The heat transmitting medium 72B has heat conductivity higher than that of the shape-memory member 20. For example, the inducing member 30 has heat conductivity higher than that of the shape-memory member 20, and the heat transmitting medium 72B has heat conductivity higher than that of the inducing member 30.

The heat transmitting medium 72B has flexibility, and is easily deformed when mechanical force is applied. When mechanical force is applied along a longitudinal axis of the heat transmitting medium 72B, a folded-back section 72Bc moves along the longitudinal axis.

The cooling system 70B further includes a fixing member 74B that fixes a first end 72Ba of the heat transmitting medium 72B, a force generating device 76B that generates mechanical force along the longitudinal axis of the heat transmitting medium 72B, and a force transmitting member 78B that transmits the mechanical force generated by the force generating device 76B to the heat transmitting medium 72B. The force transmitting member 78B is mechanically fixed to a second end 72Bb of the heat transmitting medium 72B, and is moved along the longitudinal axis of the heat transmitting medium 72B by the force generating device 76B.

When the heat transmitting medium 72B is evacuated from the inducing member 30, there are a gap between the shape-memory member 20 and the inducing member 30, and a gap between the inducing member 30 and the heat transmitting medium 72B, as shown in FIGS. 8 and 9.

If the second end 72Bb of the heat transmitting medium 72B is pushed out by the force generating device 76B (that is, moved in a direction to come closer to the inducing member 30), the folded-back section 72Bc of the heat transmitting medium 72B first abuts the inducing member 30, and then moves over the inducing member 30. Consequently, the heat transmitting medium 72B comes into contact with the inducing member 30; furthermore, a diameter of the inducing member 30 is decreased, and the inducing member 30 comes into contact with the shape-memory member 20. As a result, the gap between the inducing member 30 and the heat transmitting medium 72B and the gap between the shape-memory member 20 and the inducing member 30, as shown in FIGS. 10 and 11 disappear.

In contrast, if the second end 72Bb of the heat transmitting medium 72B is pulled back by the force generating device 76B (that is, moved in a direction to move away from the inducing member 30), the folded-back section 72Bc of the heat transmitting medium 72B moves on the inducing member 30, and eventually moves away from the inducing member 30. As a result, a gap is generated between the shape-memory member 20 and the inducing member 30, and a gap is also generated between the inducing member 30 and the heat transmitting medium 72B, as shown in FIGS. 8 and 9.

As described above, the cooling system 70B switches between a contact or non-contact state of the heat transmitting medium 72B with the inducing member 30 by deforming the heat transmitting medium 72B by applying mechanical force to the heat transmitting medium 72B, more specifically, by moving the heat transmitting medium 72B along the longitudinal axis of the shape-memory member 20 through the force transmitting member 78B.

The heat dissipation efficiency of the shape-memory member 20 is higher in a situation in which the shape-memory member 20, the inducing member 30, and the heat transmitting medium 72B are mechanically in contact with each other than in a situation in which the shape-memory member 20, the inducing member 30, and the heat transmitting medium 72B are mechanically separate from each other. That is, the heat dissipation efficiency of the shape-memory member 20 is switched by switching a contact or non-contact state of the heat transmitting medium 72B with the inducing member 30 by the cooling system 70B.

When switching the variable-stiffness actuator 10B from a rigid state to a flexible state, the heat transmitting medium 72B is brought into contact with the inducing member 30 by the cooling system 70B, so that the time required for transition to the flexible state is shortened.

In the present embodiment, since the inducing member 30 is arranged around the outside of the shape-memory member 20, the heat transmitting medium 72B is brought into contact with the inducing member 30 by the cooling system 70B, but the heat transmitting medium 72B may be brought into contact with the shape-memory member 20, similar to the second embodiment.

Fourth Embodiment

Figure 12:
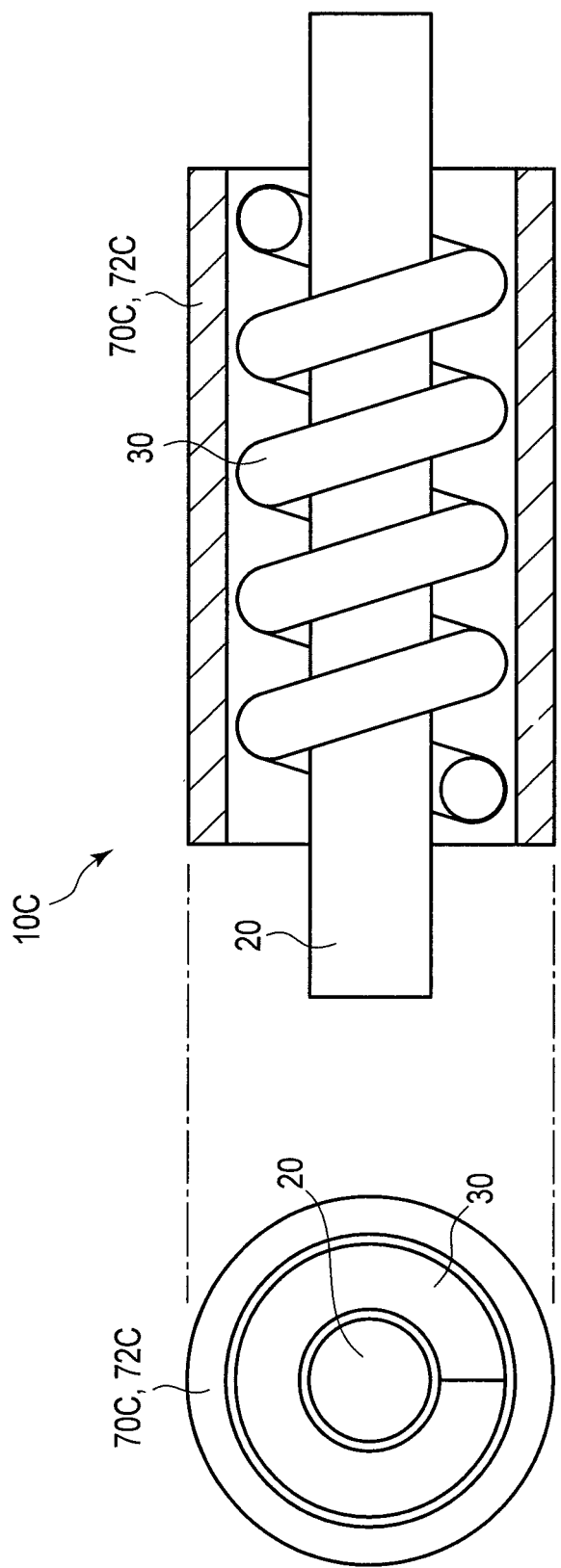
FIG. 12 shows a variable-stiffness actuator according to a fourth embodiment when a heat transmitting medium is in a first phase.

FIGS. 12 and 13 show a variable-stiffness actuator according to a fourth embodiment. In FIGS. 12 and 13, the members identical to those shown in FIG. 1 are assigned the reference numerals identical to those shown in FIG. 1, and the detailed descriptions thereof are omitted. In the drawings of the fourth and subsequent embodiments, the controller 50, wires 62 and 64, and insulating films 42 and 44 are not shown to simplify the drawings. The following descriptions will be provided with an emphasis on the difference. Namely, the points that are not mentioned below are the same as those of the first embodiment.

FIG. 12 shows a variable-stiffness actuator 100 when a heat transmitting medium 72C is in a first phase. FIG. 13 shows the variable-stiffness actuator 100 when the heat transmitting medium 72C is in a second phase.

The variable-stiffness actuator 100 of the present embodiment includes the shape-memory member 20, the inducing member 30, and a cooling system 70C that cools the shape-memory member 20.

The cooling system 70C includes a heat transmitting medium 72C that promotes heat dissipation from the shape-memory member 20. The heat transmitting medium 72C is arranged around the outside of the inducing member 30, and extends along a longitudinal axis of the shape-memory member 20. That is, the heat transmitting medium 72C has a hollow shape such as a cylindrical shape, and the shape-memory member 20 and the inducing member 30 are arranged in an inner space of the heat transmitting medium 72C.

The heat transmitting medium 72C has heat conductivity higher than that of the shape-memory member 20. For example, the inducing member 30 has heat conductivity higher than that of the shape-memory member 20, and the heat transmitting medium 72C has heat conductivity higher than that of the inducing member 30.

The heat transmitting medium 72C is made from a shape-memory material that is deformed in accordance with a temperature change, such as a shape-memory alloy. The heat transmitting medium 72C memorizes a shape with a large diameter as shown in FIG. 12 when the heat transmitting medium 72C is in the first phase lower than a transformation temperature. The heat transmitting medium 72C memorizes a shape with a small diameter as shown in FIG. 13 when the heat transmitting medium 72C is in the second phase higher than the transformation temperature. The material selection is performed so that the transformation temperature of the heat transmitting medium 72C is lower than a transformation temperature of the shape-memory member 20.

When the heat transmitting medium 72C is in the first phase, there are a gap between the shape-memory member 20 and the inducing member 30, and a gap between the inducing member 30 and the heat transmitting medium 72C, as shown in FIG. 12.

If the temperature of the heat transmitting medium 72C exceeds the transformation temperature by the heat generation of the inducing member 30, the heat transmitting medium 72C transitions from the first phase to the second phase, and decreases its diameter. Consequently, the heat transmitting medium 72C comes into contact with the inducing member 30; furthermore, reduction of the diameter of the heat transmitting medium 72C decreases a diameter of the inducing member 30, and then the inducing member 30 comes into contact with the shape-memory member 20. As a result, the gap between the inducing member 30 and the heat transmitting medium 72C, and the gap between the shape-memory member 20 and the inducing member 30 disappear, as shown in FIG. 13.

In contrast, if the temperature of the heat transmitting medium 72C decreases and becomes lower than the transformation temperature, the heat transmitting medium 72C transitions from the second phase to the first phase, and increases its diameter. As a result, a gap is generated between the shape-memory member 20 and the inducing member 30, and a gap is also generated between the inducing member 30 and the heat transmitting medium 72C, as shown in FIG. 12.

As described above, a contact and non-contact state of the heat transmitting medium 72C with the inducing member 30 is switched in accordance with a temperature change.

The heat dissipation efficiency of the shape-memory member 20 is higher in a situation in which the shape-memory member 20, the inducing member 30, and the heat transmitting medium 72C are mechanically in contact with each other than in a situation in which the shape-memory member 20, the inducing member 30, and the heat transmitting medium 72C are mechanically separate from each other. That is, the heat dissipation efficiency of the shape-memory member 20 is switched by switching a contact or non-contact state of the heat transmitting medium 72C with the inducing member 30 by the cooling system 70C.

When switching the variable-stiffness actuator 10C from a rigid state to a flexible state, the heat transmitting medium 72C contacts the inducing member 30, so that the time required for transition to the flexible state is shortened.

In the present embodiment, since the inducing member 30 is arranged around the outside of the shape-memory member 20, the heat transmitting medium 72C is brought into contact with the inducing member 30 by the cooling system 70C, but the heat transmitting medium 72C may be brought into contact with the shape-memory member 20 similarly to the second embodiment.

Fifth Embodiment

Figure 14:
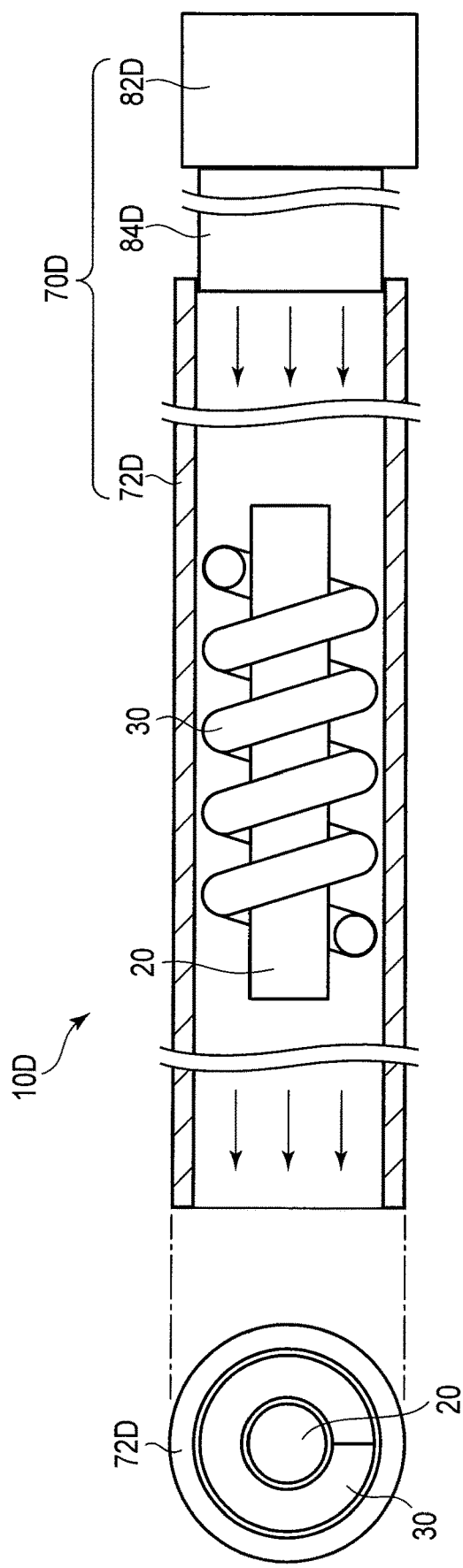
FIG. 14 shows a variable-stiffness actuator according to a fifth embodiment.

FIG. 14 shows a variable-stiffness actuator according to a fifth embodiment. In FIG. 14, the members identical to those shown in FIG. 1 are assigned the reference numerals identical to those shown in FIG. 1, and the detailed descriptions thereof are omitted. The following descriptions will be provided with an emphasis on the difference. Namely, the points that are not mentioned below are the same as those of the first embodiment.

A variable-stiffness actuator 10D of the present embodiment includes the shape-memory member 20, the inducing member 30, and a cooling system 70D that cools the shape-memory member 20.

The cooling system 70D includes a heat transmitting medium 72D that promotes heat dissipation from the shape-memory member 20. The heat transmitting medium 72D is arranged around the outside of the inducing member 30, and extends along a longitudinal axis of the shape-memory member 20. That is, the heat transmitting medium 72D has a hollow shape such as a cylindrical shape, and the shape-memory member 20 and the inducing member 30 are arranged in an inner space of the heat transmitting medium 72D.

The heat transmitting medium 72D has heat conductivity higher than that of the shape-memory member 20.

The cooling system 70D further includes a fluid supplying source 82D that supplies a fluid, and a fluid path 84D that fluidically connects inner spaces of the fluid supplying source 82D and the heat transmitting medium 72D. The fluid may be, for example, a gas or a liquid. The fluid supplying source 82D may be constituted by, for example, a compressor or a pump.

The fluid supplied from the fluid supplying source 82D flows into the inner space of the heat transmitting medium 72D through the fluid path 84D, and passes through the inner space of the heat transmitting medium 72D as indicated by the arrows. At this time, part of the heat of the shape-memory member 20 is transmitted to the fluid, so that the shape-memory member 20 is cooled. Part of the heat of the fluid is transmitted to the heat transmitting medium 72D, and part of the heat of the heat transmitting medium 72D is emitted to the peripheral space.

As described above, the cooling system 70D cools the shape-memory member 20 by supplying a fluid to the inner space of the heat transmitting medium 72D. Accordingly, the temperature of the shape-memory member 20 decreases to a predetermined temperature in a shorter time when a fluid is supplied to the inner space of the heat transmitting medium 72D than when a fluid is not supplied to the inner space of the heat transmitting medium 72D.

When switching the variable-stiffness actuator 10D from a rigid state to a flexible state, a fluid is supplied to the inner space of the heat transmitting medium 72D by the cooling system 70D, so that the time required for transition to the flexible state is shortened.

Sixth Embodiment

Figure 15:
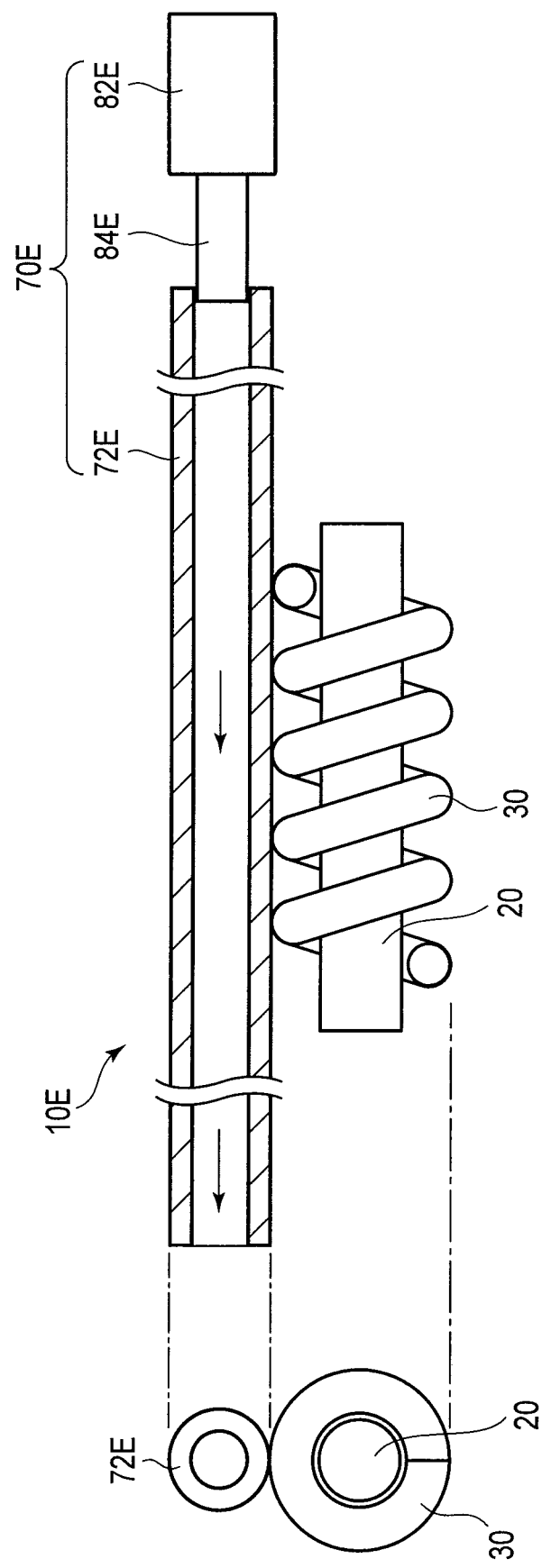
FIG. 15 shows a variable-stiffness actuator according to a sixth embodiment.

FIG. 15 shows a variable-stiffness actuator according to a sixth embodiment. In FIG. 15, the members identical to those shown in FIG. 1 are assigned the reference numerals identical to those shown in FIG. 1, and the detailed descriptions thereof are omitted. The following descriptions will be provided with an emphasis on the difference. Namely, the points that are not mentioned below are the same as those of the first embodiment.

A variable-stiffness actuator 10E of the present embodiment includes the shape-memory member 20, the inducing member 30, and a cooling system 70E that cools the shape-memory member 20.

The cooling system 70E includes a heat transmitting medium 72E that promotes heat dissipation from the shape-memory member 20. The heat transmitting medium 72E has a hollow shape such as a cylindrical shape. The shape-memory member 20 and the inducing member 30 are arranged outside and near the heat transmitting medium 72E. The heat transmitting medium 72E extends along a longitudinal axis of the shape-memory member 20. Preferably, the heat transmitting medium 72E is arranged adjacently to, for example, in contact with, the inducing member 30.

The heat transmitting medium 72E has heat conductivity higher than that of the shape-memory member 20. For example, the inducing member 30 has heat conductivity higher than that of the shape-memory member 20, and the heat transmitting medium 72E has heat conductivity higher than that of the inducing member 30.

The cooling system 70E further includes a fluid supplying source 82E that supplies a fluid, and a fluid path 84E that fluidically connects inner spaces of the fluid supplying source 82E and the heat transmitting medium 72E. The fluid may be, for example, a gas or a liquid. The fluid supplying source 82E may be constituted by, for example, a compressor or a pump.

The fluid supplied from the fluid supplying source 82E flows into the inner space of the heat transmitting medium 72E through the fluid path 84E, and passes through the inner space of the heat transmitting medium 72E as indicated by the arrows. Part of the heat of the shape-memory member 20 is transmitted to the heat transmitting medium 72E, part of the heat of the heat transmitting medium 72E is emitted to the peripheral space, and other part of the heat of the heat transmitting medium 72E is transmitted to the fluid.

As described above, the cooling system 70E cools the shape-memory member 20 by supplying a fluid to the inner space of the heat transmitting medium 72E. Accordingly, the temperature of the shape-memory member 20 decreases to a predetermined temperature in a shorter time when a fluid is supplied to the inner space of the heat transmitting medium 72E than when a fluid is not supplied to the inner space of the heat transmitting medium 72E.

When switching the variable-stiffness actuator 10E from a rigid state to a flexible state, a fluid is supplied to the inner space of the heat transmitting medium 72E by the cooling system 70E, so that the time required for transition to the flexible state is shortened.

If the variable-stiffness actuator 10E is installed in an endoscope, the heat transmitting medium 72E may be constituted by a tube member of the endoscope that guides a fluid, such as an air pipe or a water pipe.

Seventh Embodiment

Figure 16:
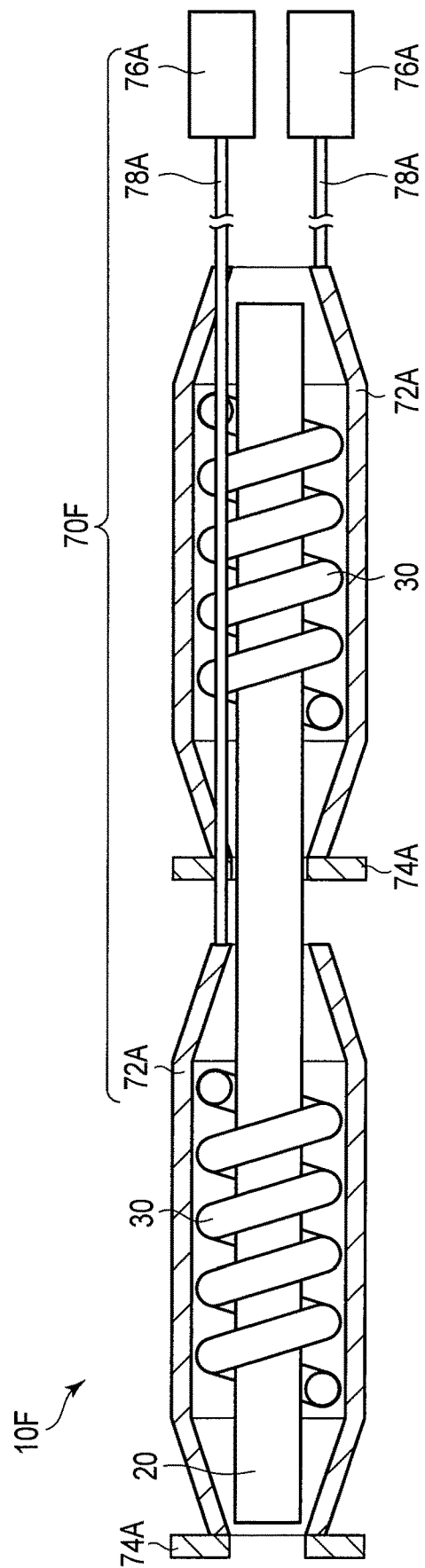
FIG. 16 shows a variable-stiffness actuator according to a seventh embodiment.

FIG. 16 shows a variable-stiffness actuator according to a seventh embodiment. In FIG. 16, the members identical to those shown in FIG. 1 are assigned the reference numerals identical to those shown in FIG. 1, and the detailed descriptions thereof are omitted. Namely, the points that are not mentioned below are the same as those of the first embodiment.

A variable-stiffness actuator 10F of the present embodiment includes the shape-memory member 20, inducing members 30, and a cooling system 70F that cools the shape-memory member 20.

The inducing members 30 are arranged around the outside of the shape-memory member 20, and are arranged at an interval along the longitudinal axis of the shape-memory member 20.

The cooling system 70F includes heat transmitting media 72A that promote heat dissipation respectively from portions of the shape-memory member 20, fixing members 74A that each fix an end of each of the heat transmitting media 72A, force generating devices 76A that generate mechanical force respectively along the longitudinal axes of the heat transmitting media 72A, and force transmitting members 78A that transmit the mechanical force generated by the force generating devices 76A respectively to the heat transmitting media 72A.

The function of the structure constituted by a heat transmitting medium 72A, a fixing member 74A, a force generating device 76A, and a force transmitting member 78A that are associated with each other is the same as the function of the cooling system 70A of the second embodiment. In other words, the cooling system 70F is constituted by cooling systems each equivalent to the cooling system 70A of the second embodiment, and the cooling systems are capable of operating independently from each other. Accordingly, the cooling system 70F may independently cool portions of the shape-memory member 20 on which the inducing members 30 are provided.

Accordingly, when a portion of the shape-memory member 20 on which each inducing member 30 is provided is switched from a rigid state to a flexible state, each heat transmitting medium 72A is independently brought into contact with each inducing member 30 by the cooling system 70F, so that the time required for transition to the flexible state is shortened.

The present embodiment describes a configuration example in which the variable-stiffness actuator 10F includes two inducing members 30, and the cooling system 70F includes two cooling systems each equivalent to the cooling system 70A of the second embodiment. However, the variable-stiffness actuator 10F may include three or more inducing members 30, and the cooling system 70F may include cooling systems each equivalent to the cooling system 70A of the second embodiment, the number of the cooling systems being equal to that of the inducing members 30.

Furthermore, the cooling system 70F may be constituted by cooling systems each equivalent to the cooling systems 70 and 70B to 70E other than the cooling system of the second embodiment.

Eighth Embodiment

Figure 17:
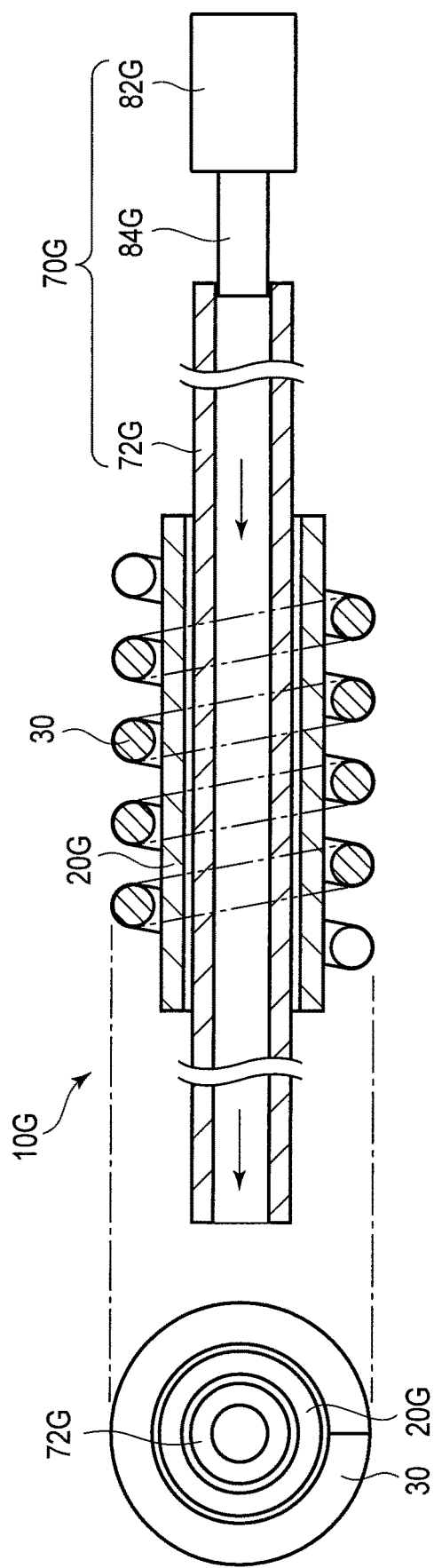
FIG. 17 shows a variable-stiffness actuator according to an eighth embodiment.

FIG. 17 shows a variable-stiffness actuator according to an eighth embodiment. In FIG. 17, the members identical to those shown in FIG. 1 are assigned the reference numerals identical to those shown in FIG. 1, and the detailed descriptions thereof are omitted. The following descriptions will be provided with an emphasis on the difference. Namely, the points that are not mentioned below are the same as those of the first embodiment.

A variable-stiffness actuator 10G of the present embodiment includes a shape-memory member 20G that can transition in phase between a first phase and a second phase, an inducing member 30 arranged around the outside of the shape-memory member 20G, and a cooling system 70G that cools the shape-memory member 20G.

The shape-memory member 20G is similar to the shape-memory member 20 of the first embodiment except for the difference in shape.

The cooling system 70G includes a heat transmitting medium 72G that promotes heat dissipation from the shape-memory member 20G. The heat transmitting medium 72G has a hollow shape such as a cylindrical shape. The heat transmitting medium 72G extends through an inner space of the shape-memory member 20G. The heat transmitting medium 72G extends along a longitudinal axis of the shape-memory member 20G.

The heat transmitting medium 72G has heat conductivity higher than that of the shape-memory member 20G.

The cooling system 70G further includes a fluid supplying source 82G that supplies a fluid, and a fluid path 84G that fluidically connects inner spaces of the fluid supplying source 82G and the heat transmitting medium 72G. The fluid may be, for example, a gas or a liquid. The fluid supplying source 82G may be constituted by, for example, a compressor or a pump.

The fluid supplied from the fluid supplying source 82G flows into the inner space of the heat transmitting medium 72G through the fluid path 84G, and passes through the inner space of the heat transmitting medium 72G as indicated by the arrows. Part of the heat of the shape-memory member 20G is transmitted to the heat transmitting medium 72G, part of the heat of the heat transmitting medium 72G is emitted to the peripheral space, and other part of the heat of the heat transmitting medium 72G is transmitted to the fluid.

As described above, the cooling system 70G cools the shape-memory member 20G by supplying a fluid to the inner space of the heat transmitting medium 72G. Accordingly, the temperature of the shape-memory member 20G decreases to a predetermined temperature in a shorter time when a fluid is supplied to the inner space of the heat transmitting medium 72G than when a fluid is not supplied to the inner space of the heat transmitting medium 72G.

When switching the variable-stiffness actuator 10G from a rigid state to a flexible state, a fluid is supplied to the inner space of the heat transmitting medium 72G by the cooling system 70G, so that the time required for transition to the flexible state is shortened.

Ninth Embodiment

FIG. 18 shows a variable-stiffness actuator according to a ninth embodiment. In FIG. 18, the members identical to those shown in FIG. 1 are assigned the reference numerals identical to those shown in FIG. 1, and the detailed descriptions thereof are omitted. The following descriptions will be provided with an emphasis on the difference. Namely, the points that are not mentioned below are the same as those of the first embodiment.

A variable-stiffness actuator 10H of the present embodiment includes shape-memory members 20H that can transition in phase between a first phase and a second phase and are shaped like wires, an inducing member 30 arranged around the shape-memory members 20H, and a cooling system 70H that cools the shape-memory members 20H.

The shape-memory members 20H are arranged, for example, on a circumference. The characteristics of the shape-memory members 20H are similar to the characteristics of the shape-memory member 20 of the first embodiment.

The cooling system 70H includes a heat transmitting medium 72H that promotes heat dissipation from the shape-memory members 20H. The heat transmitting medium 72H has a hollow shape such as a cylindrical shape. The heat transmitting medium 72H extends through a space surrounded by the shape-memory members 20H. The heat transmitting medium 72H extends along longitudinal axes of the shape-memory members 20H.

The heat transmitting medium 72H has heat conductivity higher than that of the shape-memory members 20H.

The cooling system 70H further includes a fluid supplying source 82H that supplies a fluid, and a fluid path 84H that fluidically connects inner spaces of the fluid supplying source 82H and the heat transmitting medium 72H. The fluid may be, for example, a gas or a liquid. The fluid supplying source 82H may be constituted by, for example, a compressor or a pump.

The fluid supplied from the fluid supplying source 82H flows into the inner space of the heat transmitting medium 72H through the fluid path 84H, and passes through the inner space of the heat transmitting medium 72H as indicated by the arrows. Part of the heat of the shape-memory members 20H is transmitted to the heat transmitting medium 72H, part of the heat of the heat transmitting medium 72H is emitted to the peripheral space, and other part of the heat of the heat transmitting medium 72H is transmitted to the fluid.

As described above, the cooling system 70H cools the shape-memory members 20H by supplying a fluid to the inner space of the heat transmitting medium 72H. Accordingly, the temperature of the shape-memory members 20H decreases to a predetermined temperature in a shorter time when a fluid is supplied to the inner space of the heat transmitting medium 72H than when a fluid is not supplied to the inner space of the heat transmitting medium 72H.

When switching the variable-stiffness actuator 10H from a rigid state to a flexible state, a fluid is supplied to the inner space of the heat transmitting medium 72H by the cooling system 70H, so that the time required for transition to the flexible state is shortened.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A variable-stiffness actuator, comprising:
   a shape-memory member having an end and an other end, the shape-memory member being configured to increase in stiffness upon being heated;
   a heating member different from the shape-memory member, the heating member being arranged to surround an outer periphery of the shape-memory member along a longitudinal axis of the shape-memory member, the heating member being configured to heat the shape-memory member, the heating member generating heat in response to supply of a current in order to heat the shape-memory member; and
   a heat transmitting medium arranged such that an inner diameter of the heat transmitting medium surrounds an outer periphery of the heating member along a longitudinal axis of the heating member, the heat transmitting medium being deformable between a first state and a second state, in the first state, the heat transmitting medium is deformed to decrease the inner diameter of the heat transmitting medium so as to come into contact with the heating member to increase cooling of the heating member, in the second state, the heat transmitting medium is deformed to increase the inner diameter so as to come out of contact with the heating member to decrease cooling of the heating member as compared to the cooling of the heating member in the first state.

2. The variable-stiffness actuator according to claim 1, wherein the shape-memory member is elongated, and the heat transmitting medium extends along the longitudinal axis of the shape-memory member.

3. The variable-stiffness actuator according to claim 1, wherein the heat transmitting medium is formed in a mesh-like shape.

4. The variable-stiffness actuator according to claim 1, wherein the heat transmitting medium is made from a shape-memory material that is deformed in accordance with a temperature change, so that the heat transmitting medium is switched between the first and second states with respect to at least one of the shape-memory member or the heating member in accordance with the temperature change.

5. The variable-stiffness actuator according to claim 1, further comprising heat transmitting media promoting heat dissipation from portions of the shape-memory member, respectively, the heat transmitting media independently cooling the portions of the shape-memory member, respectively.

6. The variable-stiffness actuator according to claim 1, wherein the heat transmitting medium has heat conductivity higher than heat conductivity of the heating member.

7. An endoscope comprising:
 an insertion section configured to be inserted into a body; and
 the variable-stiffness actuator according to claim 1 disposed in the insertion section.

8. An insertion section for use with an endoscope, the insertion section comprising:
 an exterior covering member configured to cover the insertion section; and
 the variable-stiffness actuator according to claim 1 disposed in the exterior covering member.

* * * * *